(12) United States Patent
Herlihy

(10) Patent No.: US 7,964,385 B2
(45) Date of Patent: Jun. 21, 2011

(54) ORGANIC WASTE TREATMENT SYSTEM UTILIZING VERMICOMPOSTING

(75) Inventor: Thomas E. Herlihy, Geneseo, NY (US)

(73) Assignee: RT Solutions, LLC, Genesco, NY (US)

( * ) Notice: Subject to any disclaimer, the term of this patent is extended or adjusted under 35 U.S.C. 154(b) by 999 days.

(21) Appl. No.: 11/733,535

(22) Filed: Apr. 10, 2007

(65) Prior Publication Data

US 2008/0251021 A1    Oct. 16, 2008

(51) Int. Cl.
*A62D 3/02*    (2007.01)
(52) U.S. Cl. ........................... 435/262.5; 71/9
(58) Field of Classification Search ............ 71/8, 9; 435/262, 262.5, 267; 119/6.7
See application file for complete search history.

(56) References Cited

U.S. PATENT DOCUMENTS

| | | | | |
|---|---|---|---|---|
| 5,401,291 | A * | 3/1995 | Inoue | 71/9 |
| 5,810,903 | A * | 9/1998 | Branconnier et al. | 71/9 |
| 5,820,759 | A | 10/1998 | Stewart | |
| 6,223,687 | B1 | 5/2001 | Windle | |
| 6,488,733 | B2 | 12/2002 | Kalra et al. | |
| 6,576,462 | B2 | 6/2003 | Thompson | |
| 6,838,082 | B2 | 1/2005 | Growcock et al. | |
| 6,890,438 | B2 | 5/2005 | Shankar et al. | |
| 6,982,167 | B2 | 1/2006 | Hahn et al. | |
| 7,018,831 | B2 | 3/2006 | Gitt | |
| 7,029,512 | B2 | 4/2006 | Johnson | |
| 7,141,169 | B2 | 11/2006 | Koehler | |
| 7,211,429 | B1 * | 5/2007 | Rudas | 435/262 |
| 7,892,310 | B2 * | 2/2011 | Le | 71/10 |
| 2002/0177219 | A1 * | 11/2002 | Olivier | 435/262 |
| 2010/0047866 | A1 * | 2/2010 | Borchert et al. | 435/69.1 |

OTHER PUBLICATIONS

Janice Barrett, *Putting Worms to Work*, Holstein World, p. 90, Aug. 2005.
Virginia Cuevas, *Development of Rapid, Contained Composting Technique to Manage Municipal Solid Wastes in the Philippines*, http://www.oardc.ohio-state.edu/michel/devcompostsystems.htm, pp. 1-3, Dec. 19, 2006.
Randy Tidwell, *Use of Composted Dairy Manure, Poultry Litter, and Sawdust as a Substitute for Peat Moss in Plant Growing media*, http://www.tamu-commerce.edu/agscience/res-dic/reports/tidwell.html, pp. 1-20, Dec. 19, 2006.
Nancy Tautmann and Elain Olynciw, *Compost Microorganisms*, Cornell Composting Science & Engineering, http://www.css.cornell.edu/compost/microorg.html, pp. 1-4, Dec. 19, 2006.
*Biosolids Technology Fact Sheet In-Vessel Composting of Biosolids*, United States Environmental Protection Agency, EPA 832-F-00-061, Sep. 2000.
Woods End Laboratories, Inc., *Summary Interpretation of Waste & Compost Tests*, Journal of the Woods End Research Laboratory 2006, vol. 1. No. 2, pp. 1-2.
Department of Soil Science, University of Wisconsin, Madison, *Composting: Art and Science of Organic Waste Conversion to a Valuable Soil Resource*, http://www.region18.com/composting.htm, pp. 1-11, Dec. 19, 2006.
Jacky Foo, *LISTSERV service at SUNET*, http://segate.sunet.se/cgi-bin/wa?A2=ind99&L=et-w1&H=1&P=22049, pp. 1-2, Dec. 19, 2006.
*Pathogen and Vector Attraction Reduction Requirements—Why Are There Pathogen and Vector Attraction Reduction Requirements?*, Chapter 5, EPA Guide to the Part 503 Rule, pp. 107-127.

* cited by examiner

*Primary Examiner* — Wayne Langel
(74) *Attorney, Agent, or Firm* — Brian B. Shaw, Esq.; Stephen B. Salai, Esq.; Harter Secrect & Emery LLP

(57) ABSTRACT

A system is provided for thermophilically conditioning organic wastes of a substantially predetermined composition to form a feedstock which is applied to an upper surface of a worm bed. The worm bed is maintained in a dominantly mesophilic regime, wherein vermicastings and vermicompost are selective removed from the bottom of the worm bed.

21 Claims, 8 Drawing Sheets

ORGANIC WASTE TREATMENT SYSTEM UTILIZING VERMICOMPOSTING

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

The present invention relates to a method and apparatus for the treatment of organic solid wastes and more particularly, to the treatment of organic wastes utilizing accelerated microbiological decomposition including composting and vermicomposting to convert materials into increased environmentally compatible products, including vermicastings and vermicompost.

2. Description of Related Art

U.S. Pat. No. 6,838,082 discloses a method of treating drilling fluid waste, wherein a biodegradable, low-toxicity drilling fluid is provided which enables bio-remediation of drill cuttings into a beneficial product using land spreading or farming with optional pre-treatment in bioreactors or through composting. U.S. Pat. No. 6,838,082 further discloses the mixing of drilling cuttings with sawdust, which is then transported to a bioremediation site. At the bioremediation site, the mixture of drilling cuttings and sawdust is mixed with paunch waste and then applied to windRows designed for vermicomposting.

U.S. Pat. No. 6,223,687 discloses a method by which composting and worm cultures are established in thin layers of matter in which a high density worm mass is encouraged to actively move into and attack undigested material at high rates. The thinness of the layers encourages migration to other areas and results in decreased worm stratification and increased uniformity of composting. In order to facilitate the processing of large quantities of matter in this manner, the matter is formed into thin layers on a moving surface. By controlling the surface speed to match that of worm migration through the layer of matter, a continuous process from a loading station to an unloading station can be maintained. The worms are always retained on the surface in a portion of the matter while the digested matter is removed.

However, the disposal of waste is an increasing concern both nationally and worldwide. Efforts at recovering waste composed of material which can be recycled into new usable forms have been somewhat successful, but there remains a need for a system and process which provides increased environmental compatibility, along with the capacity for the disposal of organic wastes, including paper materials, yard clippings, woody scraps, manures, sludges, select industrial residuals and feed wastes.

The need also remains for a comprehensive method and apparatus for treating organic solid wastes as well as materials containing relatively high nitrogen contents such as manures, sludges and pre and post consumer food wastes, wherein a feedstock is prepared for vermicomposting and the vermicomposting is accomplished within predetermined parameters. The need further exists for a method of adequately preparing the feedstock for vermicomposting, wherein subsequent vermicomposting is carried out with the feedstock.

BRIEF SUMMARY OF THE INVENTION

The present invention provides a system and process utilizing accelerated microbial decomposition of organic solid materials as well as at least partial composting and subsequent vermicomposting to convert organic solid wastes into more environmentally compatible products. In one configuration, the process and system are configured to substantially reduce the production or release of noxious emissions as well as chemically or biologically hazardous materials during the process. Accordingly, the present system can be located in close proximity to inhabited communities.

In one configuration, the method encompasses aerobically conditioning, in a dominantly thermophilic regime lasting at least 72 hours, a mixture of organic wastes having a carbon to nitrogen ratio between approximately 10 to 1 to as much as 60 to 1 so as to form a feedstock; applying the feedstock to a worm bed; and maintaining a temperature and humidity of the worm bed and the applied feedstock to maintain a mesophilic dominant regime within the worm bed.

In further configurations, temperature of the mixture in the thermophilic dominant regime is reduced by the circulation of air through the mixture. Further, a moisture gradient between a bottom strata of the worm bed and a top strata of the worm bed can be maintained. The moisture gradient can be maintained through the selective application of water to an upper surface of the worm bed. It is also understood a tent can be formed over the worm bed to control moisture release.

It is therefore an object of the present invention to provide an organic solid waste treatment system which allows for the efficient, economical, and environmentally compatible treatment of organic waste materials by decomposing waste mixtures using accelerated, microbiological decomposition (conditioning) to form a feedstock and then vermicomposting the feedstock to achieve commercially viable products.

It is a further object of the invention to provide an organic solid waste treatment system which sufficiently reduces the release of harmful or noxious emissions or materials such that the system can be operably located near inhabited communities.

The accompanying drawings are included to provide a further understanding of the invention, and are incorporated in and constitute a part of this specification. The drawings are not necessarily to scale, and sizes of various elements may be distorted for clarity. The drawings illustrate one or more embodiment(s) of the invention, and together with the description serve to explain the principles and operation of the invention.

BRIEF DESCRIPTION OF THE SEVERAL VIEWS OF THE DRAWING(S)

DETAILED DESCRIPTION OF THE INVENTION

The present system combines at least partial composting and vermicomposting to process various organic matter, such as organic solid wastes, into environmentally compatible and economically viable products.

"Composting" is the biological decomposition of the organic constituents of wastes under controlled conditions. As used herein "conditioning" is a composting process, wherein the conditioning incorporates at least part of the composting process. While the conditioning is part of the composting process, as the conditioning is typically not complete composting, the term conditioning is used. "Vermicomposting" is understood to be the breakdown of organic matter by the ingestion and digestion of the matter by worms. Vermicomposting also includes the collateral biotransformation of organic matter from the microbiological action, such as bacterial action inherent in such systems. Thus, vermicomposting is the process by which worms convert a feedstock to produce vermicastings, (the excrement from earthworms) and vermicompost (material altered by contact with the worms, without being excrement).

There are numerous species of worms and particularly earthworms which are commonly known as "red" worms capable of performing vermicomposting. One example is *Lumbricus rubellus*, another example is *Eisenia fetida* (changed to fetida from foetida as of 2004). The red worms used in the present system are *Esenia fetida*, however, the system is not limited to the particular species of red worm, as other types will work, depending in part upon the type of organic matter and the available sustainable environment. That is, other species of earthworm can be used in addition or instead of "red" worms such as *Eisenia fetida*. As the term is used in the present description, "worm" is intended to include all types and specie of earthworm that can be utilized in the vermicomposting of organic materials.

Figure 1:
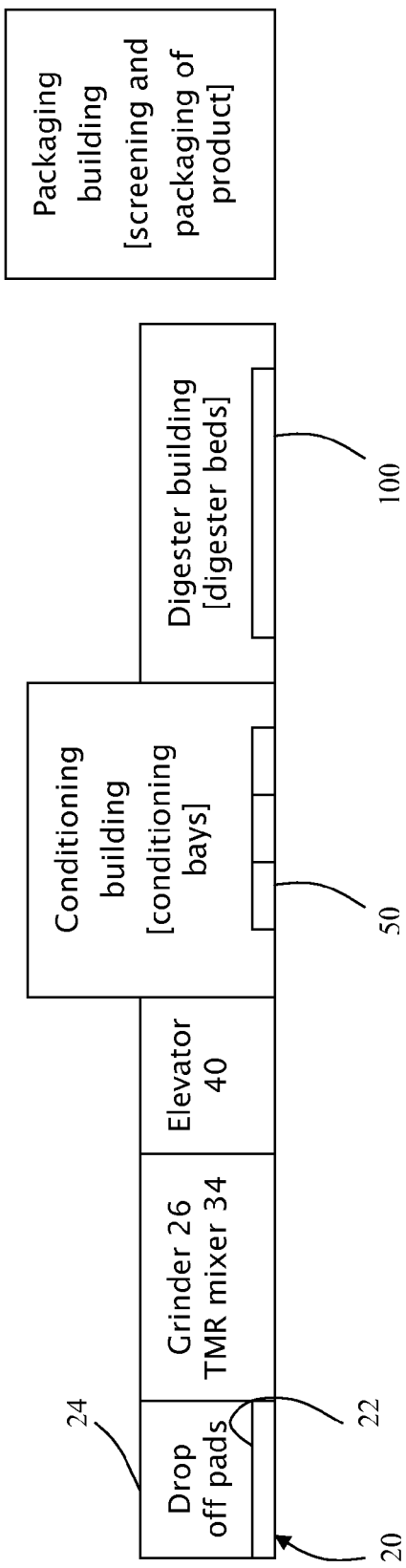
FIG. 1 is a schematic diagram illustrating a configuration of buildings for the present system.

Structurally, referring to FIG. 1, the present system includes conditioning bays 50 for conditioning (composting) and digester beds 100 for retaining worm beds supporting vermicomposting, wherein drop off pads 20 can be located upstream of the conditioning bays for stockpiling, sorting or mixing the wastes and finishing stations can be located downstream of the digester beds for rendering the products to a commercially viable state.

The drop off pads 20 are sized temporarily retain volumes of solid organic waste to be processed. The drop off pads 20 can be structured to maintain an initial condition of the wastes, and thus include a support surface 22 that is substantially water impervious, such as concrete. Further, it is advantageous for the drop off pads 20 to be covered with a roof or enclosed in a building 24 to assist in the control of processing parameters of the organic wastes. The drop off pads 20 can be sized to function as a buffer for retaining excess waste material when supply exceeds capacity and as a source when capacity exceeds supply.

Depending upon the anticipated material to be processed, a grinder 26 can be associated with the drop off pad 20. The grinder 26 is used to reduce material particle size to a size which is compatible with the downstream conditioning and vermicomposting. The grinder 26 can be any commercially available device capable of processing the intended input materials.

Figure 2:
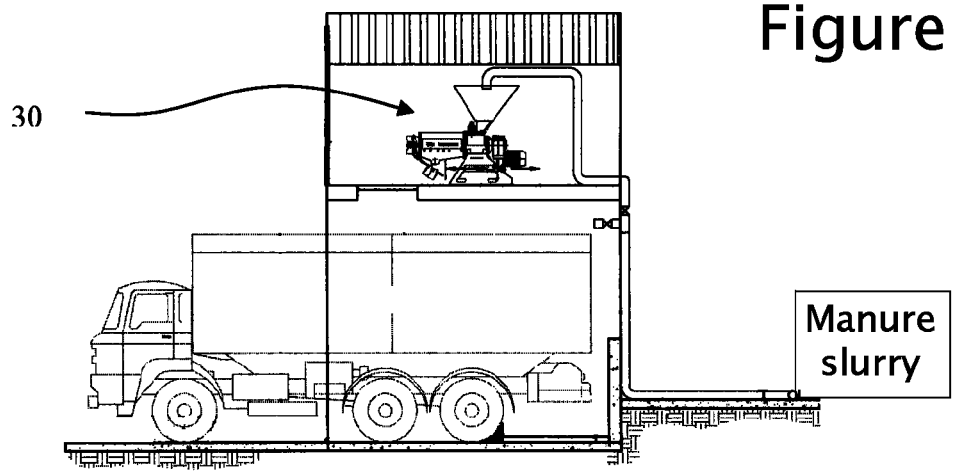
FIG. 2 is a side elevational view of a manure separator operably located relative to a truck for the generation and transport of manure solids.

In those systems for processing manure, as seen in FIG. 2, a manure separator 30 is operably located intermediate the manure source and the drop off pads 20. Typically, the manure to be processed is initially in a slurry state having approximately 10%-11% solids. The manure slurry is passed through the manure separator 30 for generally separating the manure slurry into solids and liquid components. Manure separators 30 are known in the industry and generally employ at least one horizontal rotating perforated drum screen. The manure slurry is pumped onto the drum screen sidewall. Contra-shear forces, generated by rotating the screen in the opposite direction of the input flow, shear at least a portion of the solids out of the slurry. The liquids flow through the screen and are discharged for storage or further treatment. The solids are conveyed out of the drum screen by continuous flighting. The solids are stockpiled or can be fed into a roller press, or other similar device for further dehydration. Any of a variety of commercially available manure separators 30 can be used, such as those by Accent Manufacturing, Inc. of Abbotsford, B.C., Canada.

Again, depending upon the intended material to be processed, a hydrapulper (not shown), which rehydrates dry pulp, pulps up recycled papers, and otherwise mixes and blends paper stock with water to create the desired moisture content of pulp stock, can be used for particle size reduction and mixing the wastes for composting. The hydrapulping process can also be used to provide additional moisture content to the waste materials, to reduce the size of the materials for accelerating the composting (and subsequent vermicomposting) and to further ensure the removal of material inappropriate for vermicomposting.

Referring to FIG. 1, the present system typically includes a mixer 34 associated with the conditioning bays 50. In one configuration, the mixer 34 also grinds the material, so that input material is processed to form a relatively uniform mixture, wherein the mean particle size can be adjusted to a generally predetermined size. In addition, the mixer 34 can include a scale for weighing the amount of input material, thus accurate amounts of specific waste materials can be introduced to form a mixture of a desired constituency. A satisfactory mixer 34 has been found to be a TMR vertical mixer. However, the TMR mixer can be a horizontal mixer with a single or multiple screw. The TMR includes blades for mixing and grinding as well as scales for measuring total and added weights.

A vertical conveyor 40 is located intermediate the mixer 34 and the conditioning bay 50 to transfer the mixture from the mixer to the conditioning bay, while reducing compaction of the mixture and maintaining a substantially uniform density of the mixture. Any of a variety of commercially available conveyors can be used, depending in part upon the intended volume of material to be processed.

Figure 6A:
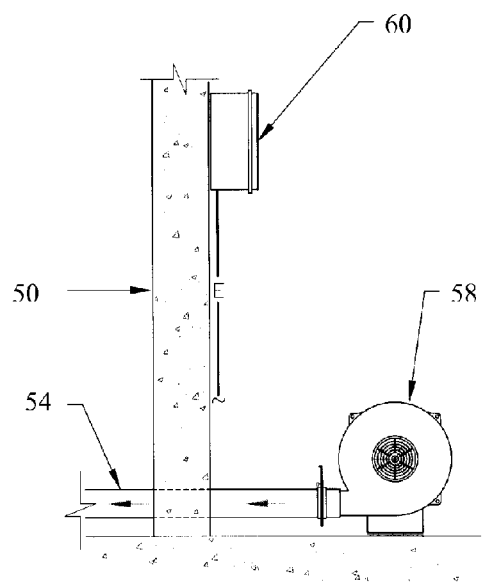
FIG. 6A is a side elevational view of an air pump and an air controller associated with the conditioning bay.
Figure 10:
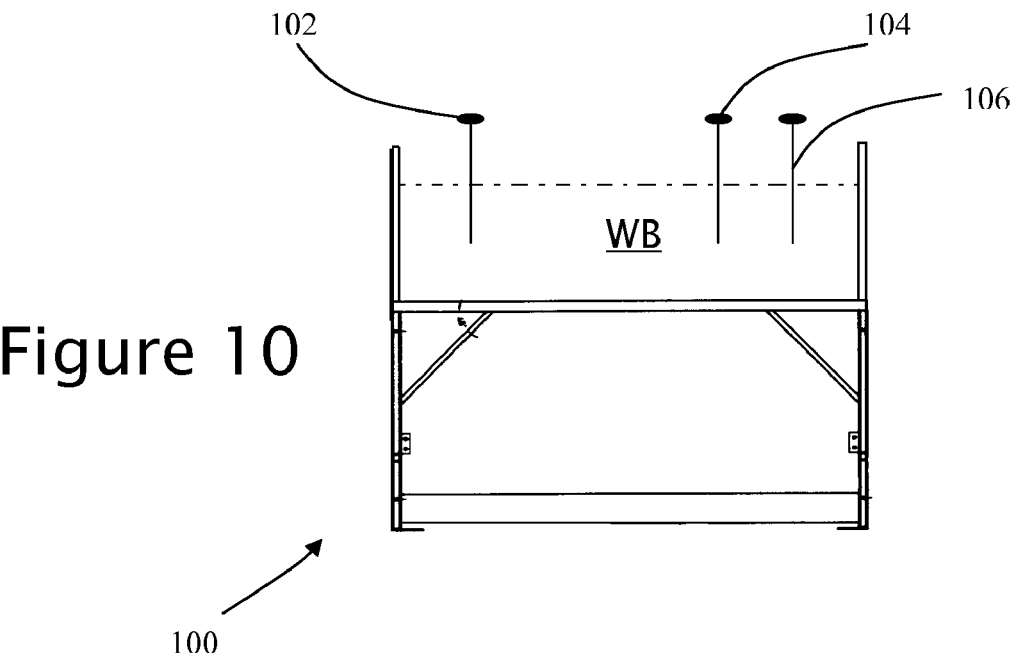
FIG. 10 is a side elevational view of a section of the digester bed of FIG. 8.

As seen in FIG. 1, the conditioning bays 50 are located downstream from the drop off pads 20. Referring to FIGS. 3-7, the conditioning bays 50 include a solid subfloor 52 and an air passing floor 56 spaced above the subfloor, wherein a plurality of air manifolds 54 are located between the subfloor and the air passing floor. The air passing floor 56 can be any of a variety of structures that can support the weight of a mixture pile, without permitting excessive amounts of the mixture to pass to the subfloor. In one configuration, the air passing floor 56 is formed of a plurality of 2"×10"×12' planks spaced approximately 0.25 inches to 0.5 inches apart. This gapping is sufficient to permit the passage of air, without allowing a detrimental amount of the mixture to pass through the floor and foul the air manifolds. That is, the gapping in the air passing floor 56 is selected to enhance bridging of the mixture above the gaps. The air manifolds 54 are fluidly connected to air pumps 58 for controlling an air flow rate through the air manifolds and hence into the conditioning bay 50. As seen in FIG. 6A, the air pumps 58 can be connected to an air controller 60 for regulating the amount of air passing through the air manifolds 54 and into the mixture in the conditioning bay 50.

The gapping in the air passing floor 56 and the air manifolds 54 are selected to provide a substantially uniform distribution of air throughout the area of the air passing floor. This uniform distribution is used in conjunction with mixtures placed on the air passing floor 56 that are substantially uniform, and thus consistent preferential flow paths are not formed in the mixture. Conversely, if the mixture deposited upon the air passing floor 56 is configured to form preferential flow paths, then the air passing floor 56 (and the air manifolds if necessary) are configured to provide a substantially equal distribution of air though the mixture.

In one configuration, the air passing floor 56 is approximately 20'×12', wherein fixed walls extend upwardly on three sides (the back and two sides) of the air passing floor to define the conditioning bay. Depending upon the intended operating parameters of the conditioning bays, the walls can extend to a height of approximately 8' to 12'. A front edge of the floor includes sockets for receiving posts for supporting a front wall so that the conditioning bay has four walls. In one configuration, the front wall is removable to allow for maintenance of the air passing floor 56 and the air manifolds 54.

The conditioning bays 50 can include temperature sensors 62, such as thermocouples, humidity or moisture sensors 64 and oxygen sensors 66 for monitoring the respective parameters of the mixture. While the sensors 62, 64, 66 can be fixed relative to the conditioning bay 50, it has been found satisfactory for the sensors to be in a probe form for manual insertion into the mixture. The air controller 60 can be operably connected either automatically or by manual input to the temperature, humidity (moisture), and oxygen sensor(s) in the mixture as well as the ambient temperature and humidity sensor(s). The air controller 60, or other system controller is operably connected to the sensors 62, 64, 66 in the conditioning bay 50, and thus can selectively regulate the amount of air passing through the mixture.

Figure 11:
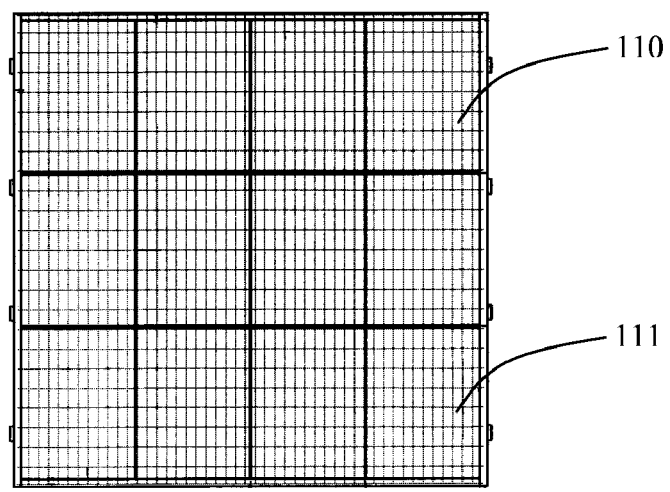
FIG. 11 is a top plan view of the section of the digester bed of FIG. 8.

The digester beds 100 are constructed to retain worm beds WB, in which reside the worms for vermicomposting. As seen in FIGS. 8-11, the digester beds 100 can be 50-350 feet long and between 4 and 12 feet wide, with walls 2 to 4 feet high. Referring to FIG. 11, the bottom of each digester bed 100 is a screen 110 with approximately 1 in$^2$ to approximately 8 in$^2$ openings 111 upon which the worm bed is supported. The openings 111 in the screen 110 are selected to allow the vermicastings and vermicompost to pass in response to an external force, while forming sufficient bridging in response to the weight of the worm bed WB so as to support the worm bed. Screen aperture sizes of less than 9.65 in$^2$ have been found satisfactory, with 2 in×2 in openings have been found advantageous.

The digester beds 100 can include temperature sensors 102, such as thermocouples, humidity or moisture sensors 104 and oxygen sensors 106 for monitoring the respective parameters of the worm bed. While the sensors 102, 104, 106 can be fixed relative to the digester bed 100, it has been found satisfactory for the sensors to be in a probe form for manual insertion into the worm bed WB.

Figure 8:
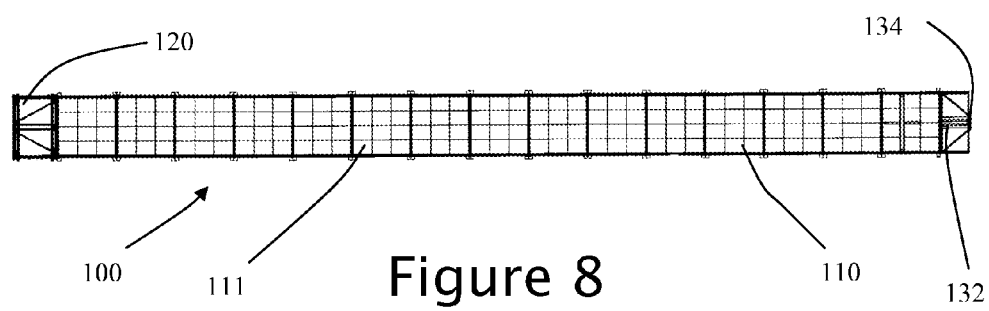
FIG. 8 is a side elevational view of a digester bed.
Figure 9:
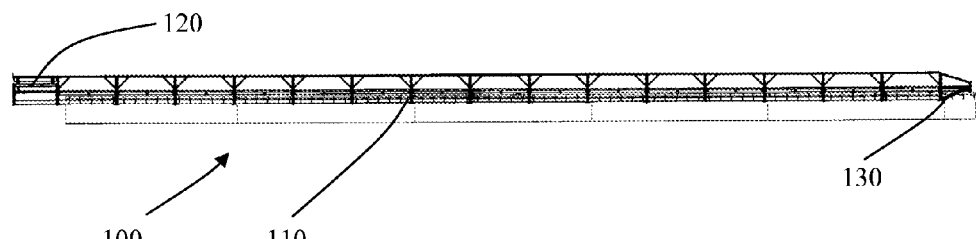
FIG. 9 is a top plan view of the digester bed of FIG. 8.

As seen in FIGS. 8 and 9, a transfer gantry 120 is movably coupled to the digester bed 100 for dispensing the conditioned mixture onto the digester beds. The transfer gantry 120 can be any of a variety of configurations for depositing a controllable layer or amount of material onto the worms bed WB in the digester bed 100.

Referring to FIGS. 8 and 9, a scraper bar 130 is translatable along the length of the digester bed 100, just above the screen 110. The scraper bar 130 is connected to a cable 132 extending to each end of the digester bed 100, wherein a winch assembly 134 is operably connected to the cable, so that by the selective winding of the cables with an associated winch, the scraper bar can be translated from end to end of the digester bed. It is understood a continuous loop of cable 132 can be employed with a single winch to translate the scraper bar 130 to each end of the digester bar 100. Alternatively, the scraper bar 130 can be hydraulically driven along the length of the digester bed 100. The scraper bar 130 is sized to urge the lowest most layer, such as approximately 1.5 inches, of the material (worm bed) in the digester bed 100 to pass through the screen to a drop zone beneath the digester bed.

As the vermicastings and vermicompost must be allowed to fall into the drop zone, the bottom of each digester bed 100 is elevated and thus spaced from the floor. This spacing below the digester bed 100 can be accomplished either by elevating the digester bed or by providing sub-floor access to the underside of the digester beds.

A commercially available barn cleaner or sweeper 140, schematically shown in FIG. 8, is disposed below the digester bed 100 in the drop zone to move the vermicastings and vermicompost from under the digester bed, so that the material can be readily collected for finishing.

A lighting system can be located beneath the digester bed 100 to flood the bottom of the worm bed WB with light. The amount, duration and intensity of the lighting can be regulated by a dedicated lighting controller. Alternatively, the control can be incorporated into another or main controller within the system.

In certain environments, it is understood the digester beds 100 are enclosed within a building, such as a digester building so that ambient temperature and humidity can be controlled. It is contemplated the control of the temperature and humidity can be directed to maintain (i) relatively constant values; (ii) values for which the amount of change can be compensated or (iii) absolute values. Typically, the digester building can include a ventilation system which, in conjunction with the controller and the available ambient temperature, regulate the environment within which the digester beds 100, and hence worm beds WB reside.

Figure 12A:
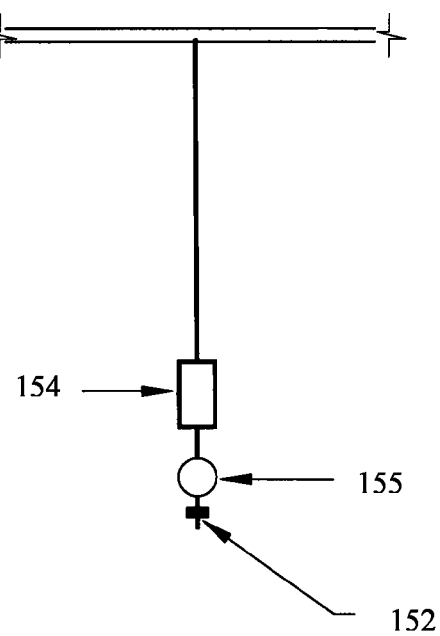
FIG. 12A is an enlarged view of a sprinkler head.
Figure 3:
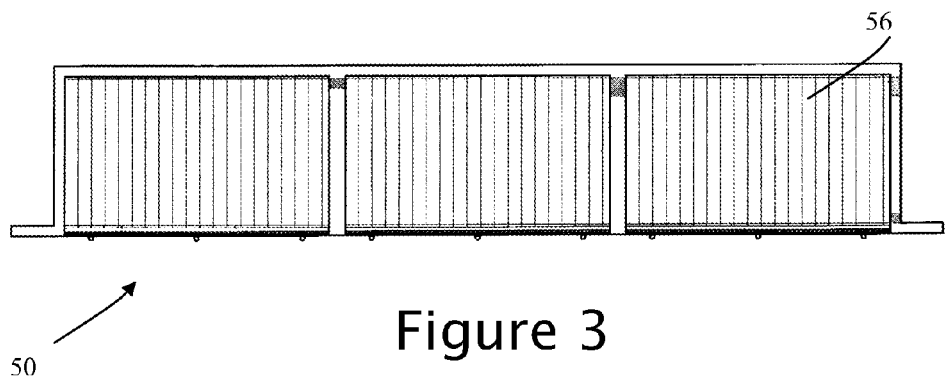
FIG. 3 is a top plan view of a set of conditioning bays.
Figure 4:
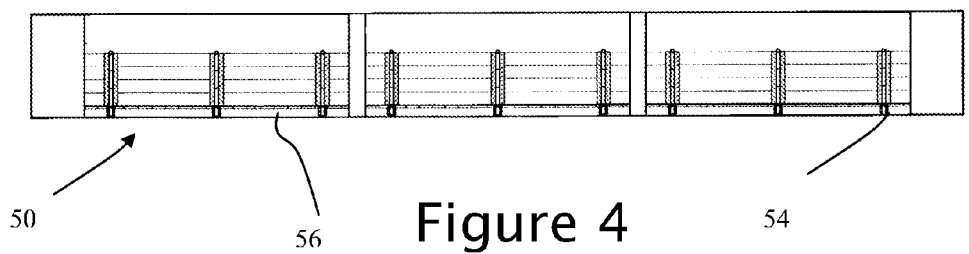
FIG. 4 is a front elevational view of the set of conditioning bays of FIG. 3.
Figure 5:
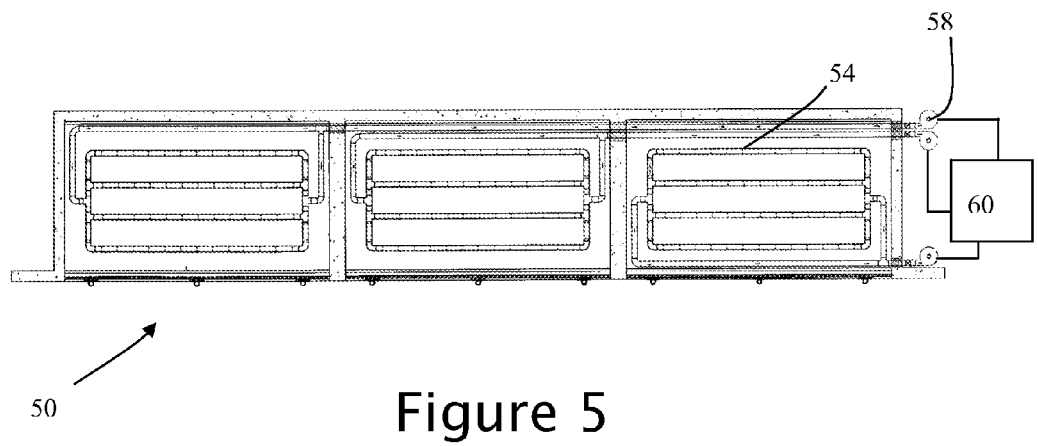
FIG. 5 is a bottom plan view of the set of conditioning bays of FIG. 3.
Figure 6:
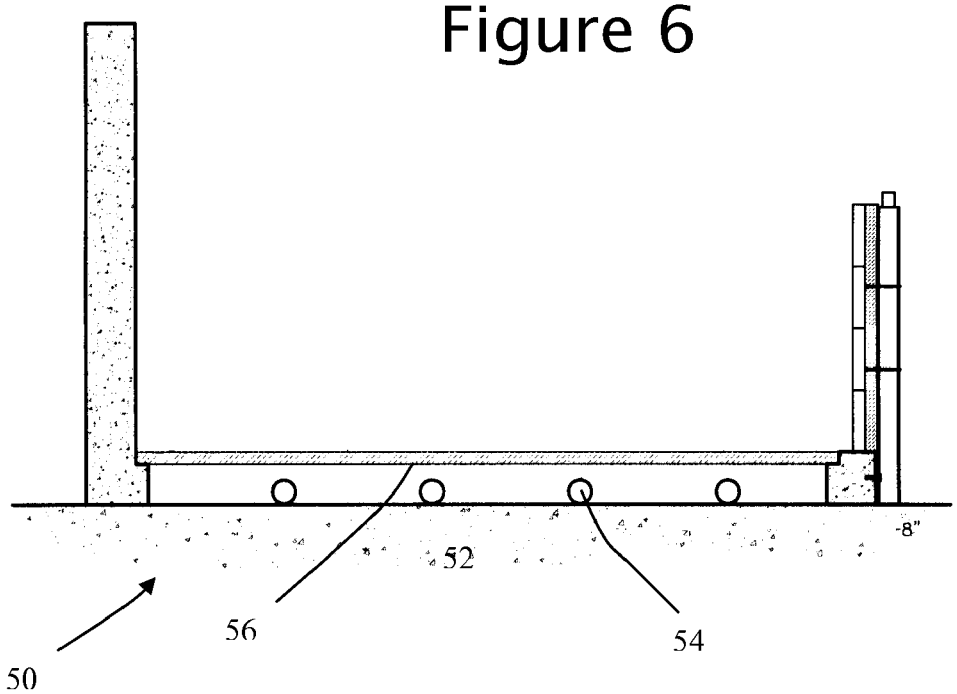
FIG. 6 is a cross sectional view of an empty conditioning bay of FIG. 3.
Figure 7:
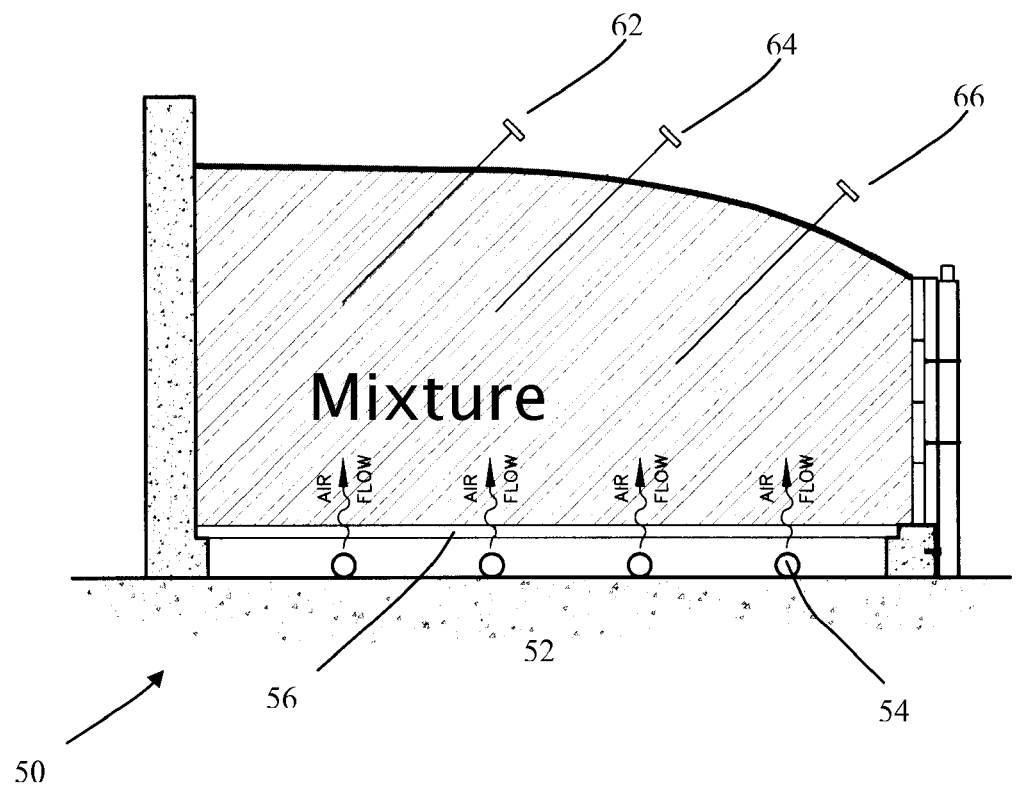
FIG. 7 is a cross sectional view of a filled conditioning bay of FIG. 3.
Figure 12:
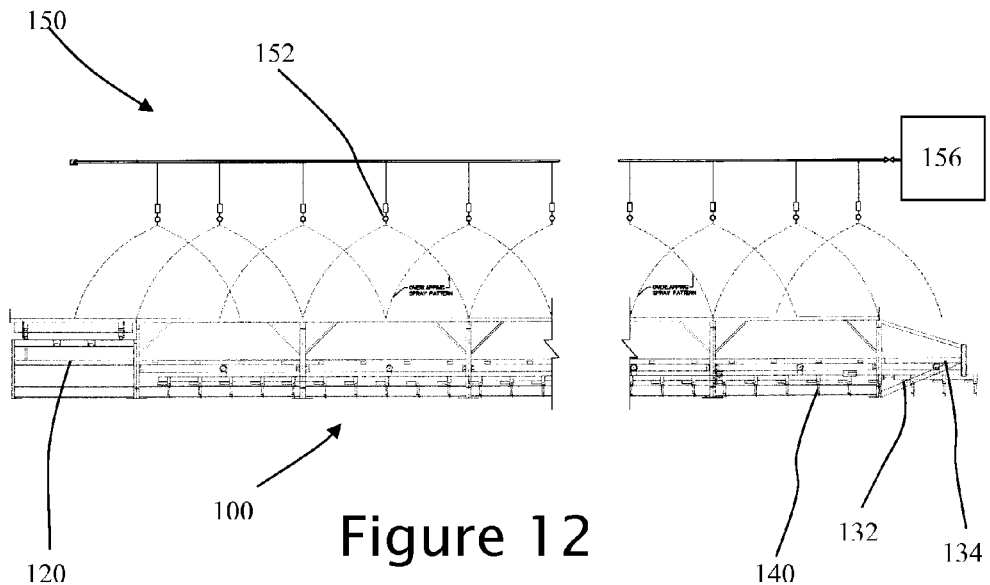
FIG. 12 is a side elevational view of a sprinkler system with a digester bed.
Figure 13:
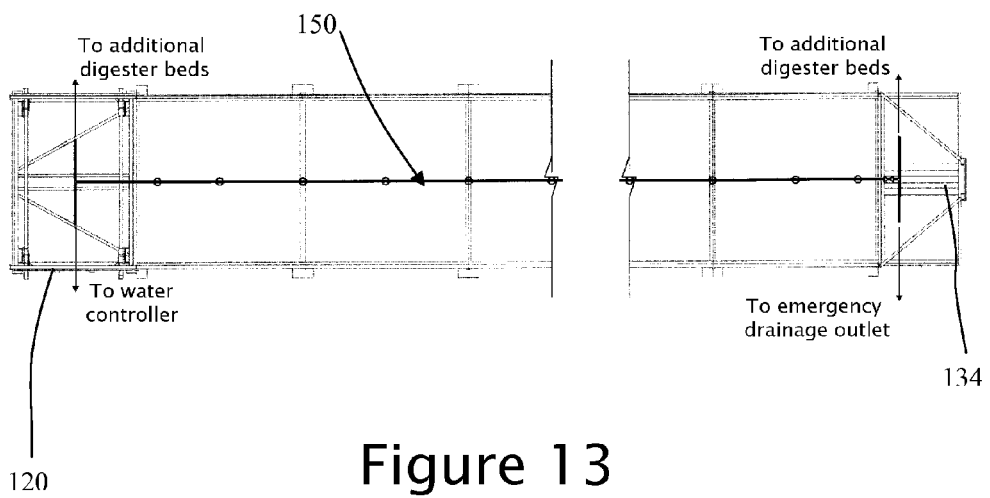
FIG. 13 is a top plan view of the sprinkler system of FIG. 12.

In addition, as seen in FIGS. 12 and 13, a sprinkler system 150 is operably associated with the digester beds 100. The sprinkler system 150 includes a water line extending from a source of water to a plurality of sprinkler heads 152, a pump connected to the water line and a water controller 156 connected to the pump. The sprinkler heads 152 are selected to create a substantially uniform distribution of water across a given pattern. However, it is understood non uniform distributions can be aligned to result in a substantially uniform distribution. The water controller 156 can be a dedicated controller or incorporated into the main system controller. The sprinkler heads 152 are oriented to apply water to a top surface of the worm bed WB. Referring to FIG. 12A, a weight stabilizer 154 can be connected to a down drop line supporting the sprinkler head 152. The weight stabilizer 154 reduces oscillations of the sprinkler head 152, which can be induced from the passage of water therethrough. Further, a check valve 155 set to a predetermined pressure can be located upstream of the sprinkler head 152 to act as a leak prevention device. That is, there must be a certain line pressure to overcome the check valve 155 and pass water to the sprinkler head 152. This reduces the risk of drowning the worms in the case of a failure of the sprinkler head to seal.

In one configuration, the source of water is at least one cistern, wherein the cistern retains collected rain water. Thus, the available water is non-chlorinated (not municipally processed). Alternatively or additionally, a well can be used to provide water to the sprinkler system. If necessary, a filtration system (not shown) can be applied to a municipal water supply to render the water compatible with the worms.

The sprinkler system 150 allows control of the timing and rate of water application to the worm bed WB. In addition, in one configuration the sprinkler heads 152 can be adjusted to vary the size of the expressed water droplet. It is further contemplated that the vertical distance between the sprinkler heads 152 and the digester bed 100 or worm bed WB can be controlled. A satisfactory height of the sprinkler heads 152 above the top of the worm bed WB has been found to be approximately 4½ feet.

The water controller 156 can be operably connected to the temperature, humidity (moisture) and oxygen sensors 102, 104, 106 in the worm bed WB as well as the ambient temperature and humidity sensors. The water controller 156, or other system controller is operably connected to the sensors 102, 104, 106 in the worm bed as well as the ambient sensors, and thus can selectively regulate the amount of water applied to the worm bed or expressed from the sprinkler heads 152.

The present system further includes a screener downstream of the digester beds 100 for sizing the vermicompost and vermicastings. Depending upon the intended use of the vermicompost and vermicastings, the screener can be used to sort two, three or more size classes of material. In one configuration, the screener separates the vermicompost and vermicastings into three categories, greater than 0.5 inches, 0.1 to 0.5 inches and less than 0.1 inches. Any of a variety of commercially available screeners can be employed.

It is contemplated the drop off pads 20, the conditioning bays 50 and the digester beds 100 can be enclosed within a common air discharge system, wherein the air discharge is passed through a biofilter. The biofilter is composed of processed material or other suitable organic matter. The biofilter reduces noxious odors emanating from the unprocessed biosolid waste in the central processing facility, and from the pre-conditioning. Alternatively, each of the drop off pads 20, the conditioning bays 50, the digester beds 100 and the screener can be located within a corresponding dedicated building.

Figure 14:
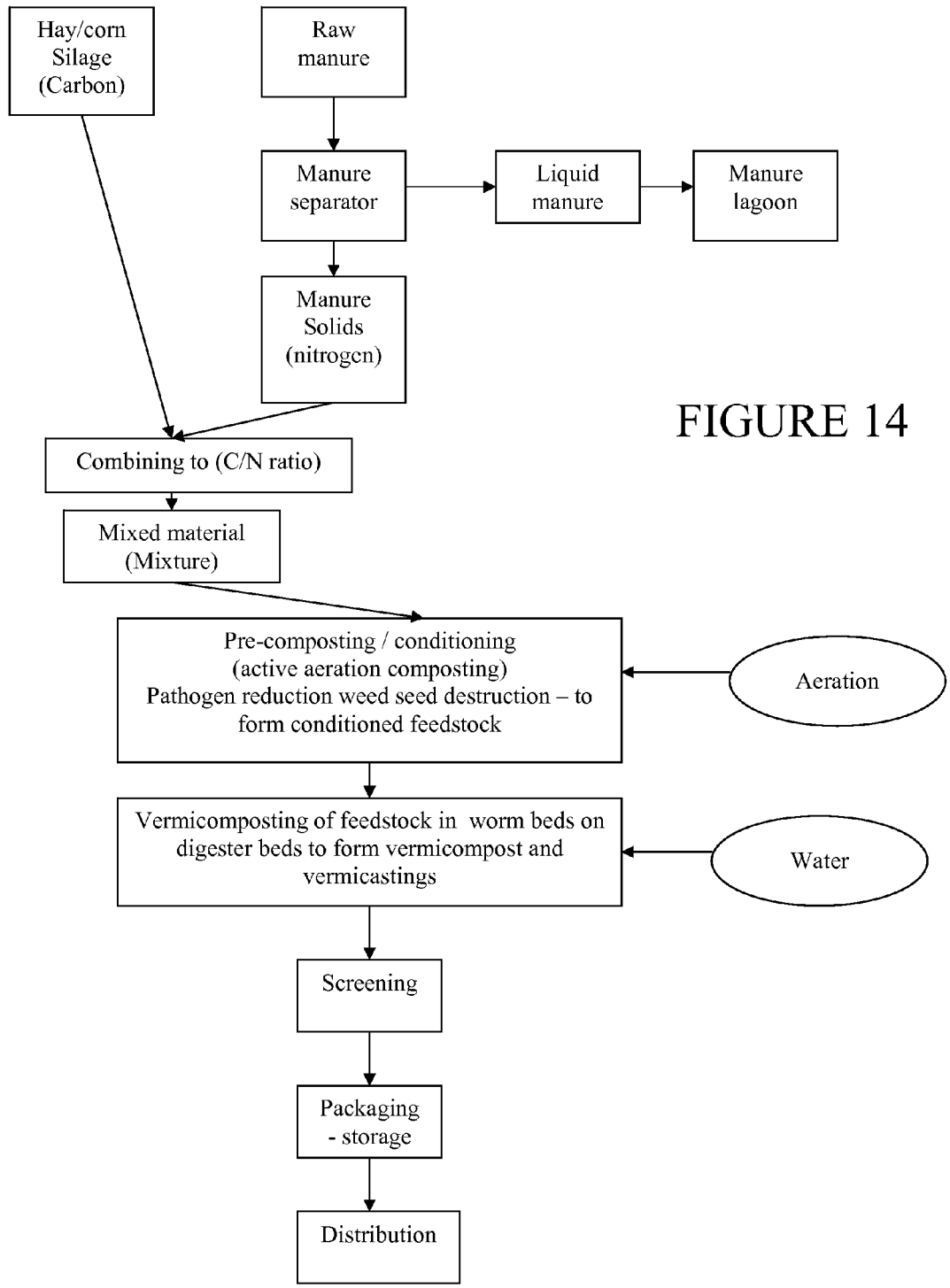
FIG. 14 is a flow diagram illustrating the various stages of the organic waste treatment system in accordance with the present invention.

Generally, as seen in FIG. 14, the process begins with the intake of various organic materials, such as solid wastes, wherein the materials are mixed to predetermined formulations, conditioned (at least partly composted) within certain parameters to form a feedstock, and the feedstock is deposited on worm beds in digester beds retaining a multitude of worms, wherein the feedstock is subjected to vermicomposting.

In one configuration, the system accepts the solid organic waste material from a variety of sources. Typically, the organic waste material is accepted at the drop off pad 20 for gross sorting and mixing. However, it is understood the gross sorting and mixing of the organic material can occur at a central processing area, wherein conventional manual and automatic sorting processes are employed to remove any remaining inorganic materials and to segregate materials requiring gross size reduction prior to alternative disposal.

The mixture to be processed is formed from the intakes. In one configuration, the mixture includes 8 parts separated manure solids, 2 parts spoiled feed and 1 part holdback (previously processed material). The separated manure solids have a solid content of at least 20% and preferable greater than 25% and in one configuration have a solid content of approximately 28%.

The mixture to be processed is generally held to predetermined parameters including bulk density, carbon to nitrogen ratio and moisture content. Typical bulk density is between approximately 600 to approximately 1,000 pounds per cubic yard, the carbon nitrogen ratio is advantageously greater than 15:1, and in certain configurations 20:1 and can be approximately 30:1. The average particle size is less than 0.75 inches and less than 0.5 inches has been found satisfactory. Of the void space in the mixture, approximately 50% is filled with water and the remaining 50% is air.

Although the present configuration is set forth in terms of separated manure solids, spoiled feed and previously processed material, it is understood other waste materials can be employed. For example, other organic wastes including biosolids, paper waste, paper mill sludges, sorted (biodegradable) municipal solid waste, MSW, can be blended together with ground woody material/yard waste.

The constituents of the mixture (the separated manure solids, scrapings and compost) are introduced into the TMR 34 and blended to provide a substantially uniform mixture having a mean particle size of approximately 0.5 inches.

The ground mixture is then conveyed by the conveyor 40 into the conditioning bay 50. In one configuration, the mixture is deposited into the conditioning bay 50 to minimize compaction and maintain a homogeneous density and degree of compaction. That is, the mixture is deposited to minimize the creation of preferential flow paths through the mixture. In one configuration, the mixture has a majority of an exposed surface area being relatively flat, thereby forming a flat topped rectangular volume within the conditioning bay 50. Thus, the deposited mixture is substantially free of preferential flow paths. Alternatively, if the conditioning bay 50 is constructed to provide preferential flow paths of the air, then the mixture is deposited in a manner corresponding to the preferential flow paths of the conditioning bay so that uniform temperature control and oxygenation can be maintained within the mixture.

In the conditioning bay 50, the mixture of blended and ground organic material undergoes forced aeration and aerobic conditioning.

The mixture initially experiences thermophilic composting. Thermophilic composting is generally within the temperature range of 104° F. (40° C.) to 158° F. (70° C.), and for the relevant microbial activity between approximately 115° F. (46° C.) to 135° F. (57° C.). In one configuration, the mixture is maintained at approximately 55° C. for at least 72 hours. During composting, heat is internally generated by the metabolic activity of microorganisms consuming putrefiable materials in the mixture. The temperature in the mixture initially rises to the thermophilic regime during the first twelve hours of the composting. In one configuration, the temperature in the mixture will rise to approximately 145° F., without the application of external heat. The maximum temperature is controlled by air circulated through the mixture from the air manifolds 54 beneath the air passing floor 56. In one process, the mixture is maintained below a maximum temperature of 180° F., and in selected configurations below approximately 170° F. However, the minimum temperature is sufficient to destroy the viability of weed seeds and provide the pathogen destruction. The air controller 60 regulates the amount of air and the timing of the air circulation to reduce and maintain the temperature within the desired range during the thermophilic process as well as ensure aesobic microbial activity. Generally, the air controller 60 operates the air pumps 58 on a timer or the sensors, and cycles on or off each thirty minute period or as the measured parameters dictate. The controlled passage of air regulates the maximum temperature of the mixture as well as introduces oxygen into the mixture to enhance aerobic activity within the mixture. The advantage of minimizing preferential flow paths through the mixture is that local regions of concentrated uncomposted waste are reduced. Thus, the presence of concentrated regions of anaerobic activity within the mixture is minimized. That is, substantially the entire mixture experiences an equivalent amount of energy conversion from aerobic composting activity.

After approximately seven to 14 days of conditioning (composting), readily available food for the microorganisms is consumed and the temperature will drop, without requiring circulation from the air manifolds, into the range of approximately 95° F.-105° F. degrees. The mixture has cycled from an ambient temperature to a thermophilic dominant temperature to a mesophilic temperature. In addition, the mixture has sequentially experienced a thermophilic bacterial dominant regime, an actinomycete dominant regime and a mesophilic fungi dominant regime. These cycles are maintained as substantially or dominantly aerobic. That is, the air controller 60 and oxygen sensor ensures that sufficient oxygen is introduced into the mixture during the cycles to substantially preclude anaerobic activity, or least maintain dominant aerobic activity. That is, anaerobic activity is suppressed by the maintaining the amount of oxygen in the mixture. The oxygen content within the mixture is typically maintained to at least 5% and advantageously to 10%.

The front wall of the conditioning bay is then removed and the mixture is re-introduced into the TMR mixer 34 and thoroughly remixed. The remixed, conditioned mixture is then redeposited into a conditioning bay 50.

The redeposited mixture then experiences a second cycle of thermophilic dominant to mesophilic dominant regime, wherein the microbial processing cycles from bacterial dominant, to actinomycete dominant to fungi dominant. This second conditioning removes additional energy from mixture. The second conditioning cycle can range from 7 to 14 days. Again, the air controller 60 and sensors monitor the re-mixture and the maximum temperature and oxygen content are regulated.

The conditioning allows an appropriate biological community of microorganisms to be developed within the mixture. This community serves two primary purposes. First, the community cultivates the appropriate microbial/fungal communities for the subsequent vermicomposting, and second, the heat generated by the community reduces or eliminates certain pathogenic organisms from the mixture.

In the feedstock (conditioned mixture), the pathogenic organisms have been reduced to below certain regulatory threshold levels. An exemplary regulatory level is 40 CFR Part 503, as amended Jul. 1, 2002. In one configuration, the mixture is subject to thermophilic regime of at least 55° C. for at least 72 hours. Generally, pathogenic organisms that may have been originally present in the input materials have been destroyed by temperature and "out-competed" by thermophilic and mesophilic microorganism growth. Further, the conditioning reduces the presence of viable weed seeds, which could otherwise contaminate the final vermicompost and vermicastings. The mixture has been biologically and physically modified, such as by temperature conditioning and energy consumption, to form the feedstock which is then transferred to the digester beds 100 for vermicomposting.

The twice conditioned mixture (feedstock) from the conditioning bays 50 can be analyzed in an audit box containing earthworms to test the suitability of the conditioned mixture to function as a feedstock and bedding material in the digester bed 100.

The feedstock is fed to the earthworms by being spread in an even thin layer, typically on the order of approximately 0.25" to 2.0" with a satisfactory depth of approximately 1.5" across the surface of the worm bed WB in the digester bed 100. The worm beds WB contain a worm mass of approximately 2-8 lbs $ft^2$ of surface area, wherein the worm mass is generally uniformly distributed in the top 6" layer of the worm bed WB.

The worms move upward through the material in the worm bed WB ingesting and/or processing the feedstock as they travel. The temperature of the worm beds WB is maintained to encourage worm travel towards the surface of the bed. That is, if the ambient temperature is too low, the worms will retreat from the surface toward a lower level in the bedding. The worm bed WB is maintained to promote a mesophilic dominant regime, without entering a thermophilic regime.

The temperature maintenance of the mesophilic regime in the worm bed WB within the digester bed 100 is a balance of at least, the amount and frequency of feedstock application, the biomass of worms in the worm bed, the amount and temperature of water applied to the worm bed and the ambient temperature. That is, the feedstock, though twice cycled through thermophilic conditioning, can self initiate a third thermophilic dominant regime upon application to the digester bed, if the mass of the applied feedstock is too great for the available worm population. Conversely, if too little feedstock is applied to the digester bed 100, there is insufficient food for the resident worms and the worm population decreases, and thus the throughput of the system decreases.

The lighting system is selectively activated to illuminate the bottom of the worm bed, thereby urging worms traveling toward the bottom of the bed to migrate upwards.

The feedstock applied to the worm bed WB is broken down in the rudimentary gizzard of the worms, further reducing the average particle size and accelerating the decomposition process. In this manner the putrefiable material is transformed in to a stable humus-like soil supplement. As additional feedstock is added to the top surface of the worm bed, the worms constantly migrate into the undigested portions of the feedstock, leaving the processed material (vermicastings and vermicompost) to be collected from the bottom of the digester bed.

The worm population is maintained indefinitely by reproduction and natural selection. Absent special circumstances, there is no need to add or remove members of the worm population beyond the initial formation of the bed. As such, the present invention is also an apparatus and process for worm production by exposing the worms to the conditioned feedstock. However, in order to maintain suitable environmental conditions for the earthworms, the biomass must be kept moist and parameters such as salinity, pH and $NH_3$ must be monitored.

The appropriate level of moisture can be achieved by the sprinkler system 150. In one configuration, a moisture gradient is maintained within the worm bed WB, wherein the bottom of the worm bed has the lowest moisture content and the top of the bed has the highest moisture content. A moisture content of approximately 55% to 85% with a content of 70% in the top 6 inches of the worm bed WB has been found satisfactory. The moisture content of the bottom of the worm bed is approximately 50%. It is also contemplated the digester bed 100, and hence worm bed WB can be at least partially overlaid with a tarp or tent to assist in moisture retention. The tarp is spaced from the top surface of the worm bed to allow air circulation, but is sufficiently close to the top surface to reduce moisture loss from the top of the worm bed WB.

Moisture content of the worm bed WB can be regulated with the sprinkler system 150. The amount of applied water is regulated to avoid a saturation that causes the worms to rise and be exposed on the surface, yet provide sufficient moisture to maintain the moisture gradient across the height of the worm bed WB. The temperature of the water to be applied is also monitored so that too much heat is not removed from or applied to the worm bed WB. That is, if the water is too cold, even though the amount of water is appropriate for moisture content, too much heat is removed and the worms migrate downwards away from the most recently applied feedstock.

The sprinkler system 150 can be adjusted to produce a fine mist above the digester bed 100, so that evaporative cooling dominates and a corresponding temperature reduction is achieved, without materially increasing the moisture content of the digester bed 100 and hence worm bed WB. That is, a substantial portion of the expressed water evaporates prior to descending to the surface of the worm bed WB and thereby locally cools the region, thus cooling the worm bed.

Thus, the worms effectively migrate upwards through the worm bed WB, always seeking a higher portion of the worm bed, having a higher food concentration (and away from the bottom illumination). As the amount and temperature of water applied to the exposed top of the worm bed WB, (digester bed 100) is regulated, the worms continually migrate upwards in the worm bed. That is, the rate of water application and the water temperature are selected to preclude driving the worms away from the surface of the worm bed WB in the digester bed 100.

The applied feedstock is processed through the worm bed WB in the digester bed 100 over a period of approximately 3-8 weeks, and typically approximately 42-45 days. As part of normal processing, the scraper bar 130 is periodically passed along the top of the screens 110 in the bottom of the digester beds 100. The bridging nature of the vermicastings and vermicompost that hold the material in place in the digester bed is disturbed and the material falls through the screen until new bridging action holds the overlying bedding in place. Material that has fallen to the drop zone is transferred to the screener, packaged and sold.

While the invention has been described in conjunction with specific exemplary embodiments thereof, it is evident that many alternatives, modifications, and variations will be apparent to those skilled in the art in light of the foregoing description. Accordingly, the present invention is intended to embrace all such alternatives, modifications, and variations as fall within the spirit and broad scope of the appended claims.

The invention claimed is:

1. A method of processing organic waste, comprising:
   (a) aerobically conditioning a mixture including separated manure solids and organic waste through a thermophilic dominant regime to a mesophilic dominant regime;
   (b) sufficiently remixing the mixture to initiate a second aerobic thermophilic dominant regime and passing the mixture to a second mesophilic dominant regime to form a feedstock;
   (c) applying the feedstock to a worm bed retained within a digester bed; and
   (d) maintaining a mesophilic dominant regime in the worm bed.

2. The method of claim 1, further comprising reducing the temperature of the mixture in the thermophilic dominant regime.

3. The method of claim 1, further comprising passing sufficient ambient air through the mixture to maintain a temperature below 180° F.

4. The method of claim 1, wherein the digester bed is a flow through digester bed.

5. The method of claim 1, further comprising maintaining a sufficient $O_2$ concentration within the mixture to substantially maintain aerobic microbiological activity.

6. The method of claim 1, further comprising maintaining a sufficient $O_2$ concentration within the mixture to substantially preclude anaerobic microbiological activity in the mixture.

7. The method of claim 1, further comprising forming the mixture into a configuration to enhance uniform flow through the mixture.

8. The method of claim 1, further comprising forming the mixture into a configuration to substantially preclude preferential flow paths through the mixture.

9. The method of claim 1, further comprising passing air through the mixture.

10. The method of claim 1, further comprising maintaining a moisture gradient between a bottom strata of the worm bed and a top strata of the worm bed.

11. The method of claim 1, further comprising grinding the mixture to provide a mean particle size less than approximately 0.5 inches before aerobically conditioning the mixture through the thermophilic dominant regime to the mesophilic dominant regime.

12. The method of claim 1, further comprising applying water to a top surface of the worm bed to maintain a moisture gradient from a top strata of the worm bed to a bottom strata of the worm bed.

13. The method of claim 1, further comprising selectively passing air through the mixture from a bottom of the mixture.

14. The method of claim 1, further comprising applying a sufficient quantity of the feedstock to the worm bed to maintain a mesophilic dominant regime within the worm bed.

15. The method of claim 1, further comprising drawing air up through the mixture.

16. The method of claim 1, further comprising maintaining a sufficient homogeneity within the mixture to substantially preclude preferential flow paths within the mixture.

17. The method of claim 1, further comprising maintaining a sufficient homogeneity within the worm bed to substantially preclude preferential flow paths within the worm bed.

18. The method of claim 1, further comprising maintaining a worm population within the worm bed of approximately 0.5 pounds to 6.0 pounds of worms per square foot of worm bed surface area.

19. The method of claim 1, further comprising applying sufficient feedstock to the worm bed to maintain a preexisting worm population within the worm bed.

20. The method of claim 1, further comprising applying sufficient feedstock to the worm bed to increase a preexisting worm population within the worm bed.

21. The method of claim 1, further comprising applying sufficient feedstock to the worm bed to decrease a preexisting worm population within the worm bed.

* * * * *

UNITED STATES PATENT AND TRADEMARK OFFICE
CERTIFICATE OF CORRECTION

| | | |
|---|---|---|
| PATENT NO. | : 7,964,385 B2 | Page 1 of 1 |
| APPLICATION NO. | : 11/733535 | |
| DATED | : June 21, 2011 | |
| INVENTOR(S) | : Thomas E. Herlihy | |

It is certified that error appears in the above-identified patent and that said Letters Patent is hereby corrected as shown below:

Title Page;
Page 1, Column 2, Paragraph (74)
Replace "Secrect"
With -- Secrest --

Signed and Sealed this
Ninth Day of August, 2011

David J. Kappos
*Director of the United States Patent and Trademark Office*